US00PP21218P3

(12) United States Plant Patent
Bijl

(10) Patent No.: US PP21,218 P3
(45) Date of Patent: Aug. 17, 2010

(54) ***NEPHROLEPIS* PLANT NAMED 'ARIANE'**

(50) Latin Name: *Nephrolepis exaltata*
Varietal Denomination: Ariane

(76) Inventor: Jacob Bijl, P.O. Box 1, 4328 ZG Burgh-Haamstede, Zld. (NL)

( * ) Notice: Subject to any disclaimer, the term of this patent is extended or adjusted under 35 U.S.C. 154(b) by 171 days.

(21) Appl. No.: 12/148,329

(22) Filed: Apr. 18, 2008

(65) Prior Publication Data

US 2009/0265824 P1 Oct. 22, 2009

(51) Int. Cl.
*A01H 5/00* (2006.01)

(52) U.S. Cl. ..... Plt./379

(58) Field of Classification Search ..... Plt./379
See application file for complete search history.

*Primary Examiner*—June Hwu

(57) ABSTRACT

A new and distinct *Nephrolepis* cultivar named 'Ariane' is disclosed, characterized by distinctive dark green foliage, hard, persistent foliage with thick main veins, strong leaf stems, resistant to breakage, and an overall strong plant habit, making for a sturdy plant for shipping and indoor ornamental usage.

1 Drawing Sheet

Figure 1:
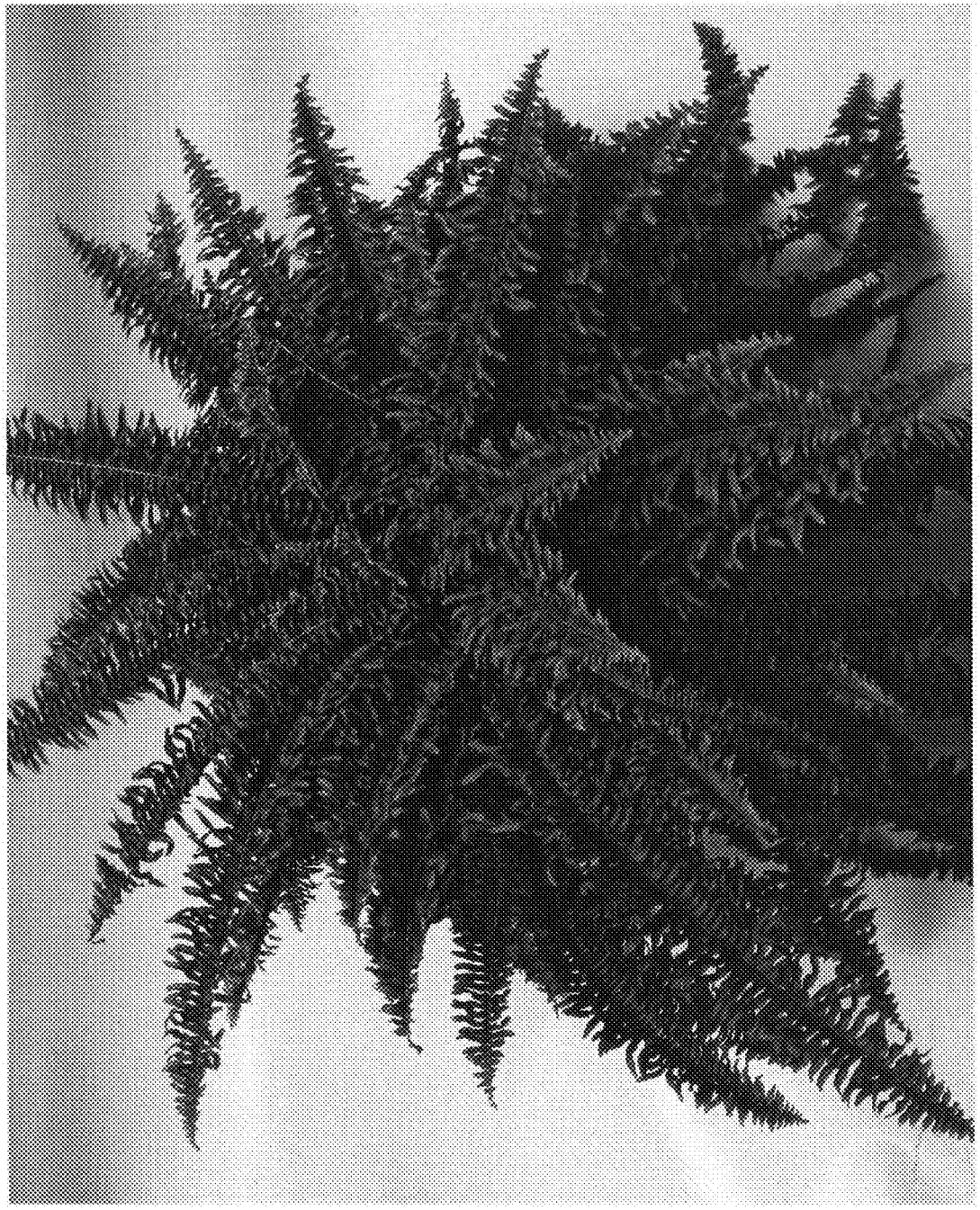

Latin name of the genus and species: *Nephrolepis exaltata.* Variety denomination: 'Ariane'.

BACKGROUND OF THE INVENTION

The new cultivar was discovered as a naturally occurring, spontaneous mutation, among a commercial planting of *Nephrolepis exaltata* var. 'Fluffy Ruffles,' unpatented.

It was discovered by the inventor, Jacob Johannes Bijl, a citizen of the Netherlands in June of 2006, at a commercial greenhouse in Zierikzee, The Netherlands. Upon discovery of the interesting mutation, the inventor initiated cultivation in tissue culture. During the summer of 2006, plants of 'Ariane' were asexually reproduced in a commercial laboratory in the Netherlands by tissue culture. Subsequently 'Ariane' has been reproduced by micro-propagation and has shown that the unique features of this cultivar are stable and reproduced true to type through several generations.

SUMMARY OF THE INVENTION

The cultivar 'Ariane' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Ariane' These characteristics in combination distinguish 'Ariane' as a new and distinct *Nephrolepis* cultivar:

1. Distinctive dark green foliage.
2. Hard foliage with thick main veins.
3. Persistent foliage.
4. Strong leaf stems, resistant to breakage.
5. Overall strong plant habit, making for a sturdy plant for shipping and indoor ornamental usage.

COMPARISON TO PARENT

Plants of the new cultivar 'Ariane' are similar to plants of the parent; *Nephrolepis exaltata* 'Fluffy Ruffles' in most horticultural characteristics, however, plants of the new cultivar 'Ariane' have a much stronger and harder leaves than the parent variety. Additionally, the new variety produces more leaves, and has foliage with a more oblong shape, whereas 'Fluffy Ruffles' produces more triangular shaped leaves. Leaves of 'Ariane' are pinnatisect whereas leaves of 'Fluffy Ruffles' are pinnate-pinnatifid. Grown side by side, 'Ariane' produces a plant of 1 meter in diameter and an average height of 45 to 50 cm, whereas 'Fluffy Ruffles' under the same growing conditions produces a plant of 75 cm in diameter and a height of 50 cm on average.

COMMERCIAL COMPARISON

The most similar commercial *Nephrolepis exaltata* variety available to compare to 'Ariane' is the parent variety, *Nephrolepis exaltata* 'Fluffy Ruffles.' However, one can also make a comparison to the commercial variety *Nephrolepis exaltata* 'Boston Compacta,' an unpatented variety. Plants of 'Boston Compact' are overall smaller and slower growing than 'Ariane.' 'Boston Compact' also produces foliage with a much more yellow coloration. Additionally, 'Ariane' differs from 'Boston Compact' in having much more crenate foliage characteristics.

BRIEF DESCRIPTION OF THE PHOTOGRAPH

The accompanying photograph in FIG. 1 illustrates in full color a typical plant of 'Ariane' grown in a greenhouse. This plant is approximately 18 months old, shown in a 1.5 liter pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Ariane' plants grown in a commercial greenhouse in the Netherlands, from November of 2006 through February of 2008.

Temperatures ranged from a minimum of 16° C. at night to 17° C. to 30° C. during the day. Measurements and numerical values represent averages of typical plant types. No growth regulators or special treatments were used.
Botanical classification: *Nephrolepis exaltata* 'Ariane.'

PROPAGATION

Time to initiate roots: Approximately 7 days at 25° C.
Root description: Creeping, well-branched and fibrous.

PLANT

Growth habit: Spreading, indoor ornamental potted plant.
Plant shape: Globose.
Height: Approximately 68 cm in a 1.5 liter pot.
Plant spread: Approximately 130 cm.
Growth rate: Moderate to rapid.
Branching characteristics: Branches emerge directly from the roots.
Frond arrangement: Alternate.
Diameter of stem: Approximately .9 cm.
Age of plant described: Approximately 18 months from a stage 3 tissue culture.

FOLIAGE

Leaf:
*Quantity per plant.*—Average 150.
*Leaf type.*—Compound Leaflets per Leaf: Average 194.
*Average Leaf length.*—Approximately 77.8 cm.
*Average Leaf width.*—Approximately 11.9 cm. Average leaflet length: Approximately 6.0 cm. Average leaflet width: Approximately 1.2 cm.
*Leaf shape.*—Linear-elliptic. Leaflet shape: Narrow lanceolate. Leaflet apex: Rounded. Leaflet base: Truncate and unequal.
*Margin.*—Crenate.
*Aspect.*—Recurved downward, slightly undulate.
*Texture of top surface.*—Smooth, moderately glossy.
*Texture of bottom surface.*—Smooth, moderately glossy.
*Pubescence.*—No pubescence of leaves or leaflets.
*Color.*—Young foliage upper side: Near R.H.S. Yellow-Green 144A. Young foliage under side: Near R.H.S. Yellow-Green 144A. Mature foliage upper side: Near R.H.S. Green 137A. Mature foliage under side: Near R.H.S. Green 137B.
*Venation.*—Type: Pinnate. Venation coloration: Uppderside: Near RHS Green 137A. Underside: Near RHS Yellow-Green 146A.
Leaf petiole:
*Length.*—5.1 cm.
*Width.*—.3 cm.
*Color.*—Near RHS Yellow-Green 146A. Underside tinged with Brown 200C.
*Texture.*—Slightly pubescent.
Leaflet petiole: Leaflets are sessile.
Other foliage characteristics: Main Rachis of each leaf is moderately covered with thick, tangled hairs.
*Length of hairs.*—Average 2.5 mm.
*Coloration of hairs.*—Near RHS Greyed-Green 197C.
*Length of rachis.*—Average 75 cm.
*Width of rachis.*—Average .3 cm.

FLOWER

Non-flowering variety.

OTHER CHARACTERISTICS

Spore production: Not detected to date.
Disease resistance: Neither resistance nor susceptibility to diseases or pests has been observed in this variety.
Temperature tolerance: Indoor tropical, hardy to at least USDA zone 10, tolerates high temperatures to at least 35° C.
Drought tolerance: No tolerance for drought.

What is claimed is:

1. A new and distinct cultivar of *Nephrolepis* plant named 'Ariane' as herein illustrated and described.

* * * * *